United States Patent
Schmidt

(10) Patent No.: US 6,989,033 B1
(45) Date of Patent: Jan. 24, 2006

(54) IMPLANT FOR RECREATING VERTERBRAE AND TUBULAR BONES

(76) Inventor: Karlheinz Schmidt, Äussere Weiler Strasse 12, D-72810 Gomaringen (DE)

( * ) Notice: Subject to any disclaimer, the term of this patent is extended or adjusted under 35 U.S.C. 154(b) by 0 days.

(21) Appl. No.: 09/958,157

(22) PCT Filed: Apr. 20, 2000

(86) PCT No.: PCT/DE00/01280

§ 371 (c)(1),
(2), (4) Date: Dec. 10, 2001

(87) PCT Pub. No.: WO00/62835

PCT Pub. Date: Oct. 26, 2000

Related U.S. Application Data

(63) Continuation-in-part of application No. 09/295,302, filed on Apr. 21, 1999, which is a continuation-in-part of application No. 08/899,270, filed on Jul. 23, 1997, now Pat. No. 5,928,635, which is a continuation of application No. 08/313,113, filed on Dec. 7, 1994, now abandoned, which is a continuation-in-part of application No. 08/350,666, filed on Dec. 7, 1994, now Pat. No. 5,932,207, which is a continuation of application No. 07/849,083, filed on Sep. 17, 1992, now abandoned.

(30) Foreign Application Priority Data

Apr. 20, 1999 (DE) .......................................... 199 17 696

(51) Int. Cl.
A61F 2/28 (2006.01)

(52) U.S. Cl. .................................. 623/23.51; 623/23.61
(58) Field of Classification Search ..... 623/23.51–23.6, 623/23.61, 23.74, 23.75, 23.76; 606/76
See application file for complete search history.

(56) References Cited

U.S. PATENT DOCUMENTS

| 4,457,984 A | 7/1984 | Otani et al. |
| 4,919,666 A | 4/1990 | Buchhorn et al. ............ 623/16 |
| 5,108,436 A | 4/1992 | Chu et al. |
| 5,139,424 A | 8/1992 | Yli-Urpo |
| 5,545,208 A | 8/1996 | Wolff et al. ..................... 623/1 |
| 5,824,651 A | 10/1998 | Nanci et al. .................. 514/21 |

FOREIGN PATENT DOCUMENTS

| CN | 2 286 032 | | 7/1998 | |
| EP | 0 615 428 | * | 3/2002 | |
| GB | 2 164 042 A | | 3/1986 | |
| GB | 2164042 | * | 3/1986 | ............. 623/23.51 |
| JP | 57-134154 | | 8/1982 | |

(Continued)

OTHER PUBLICATIONS

K. Anselme, Osteoblast adhesion on biomaterials, Biomaterials 21, 2000 pp. 667–681.

*Primary Examiner*—Pedro Philogene
(74) *Attorney, Agent, or Firm*—Blank Rome LLP

(57) ABSTRACT

The invention relates to an implant for at least partially creating, recreating or stabilizing vertebral bodies or tubular bones. In said implant, a metallic, nonmetallic or ceramic hollow body is coated with an active substance complex or comprises said active substance complex. This active substance complex comprises the following components which differ from one another and which are specifically adapted for creating bone: at least one structural component based on extracellular material which is specifically adapted to the cells of the bone which is to be created, at least one recruiting component, at least one adhesion component, and at least one growth and/or maturation component.

6 Claims, 5 Drawing Sheets

FOREIGN PATENT DOCUMENTS

| | | |
|---|---|---|
| JP | 59-211447 | 11/1984 |
| JP | A-60-253455 | 12/1985 |
| JP | A-1-151461 | 6/1989 |
| JP | A-7-008547 | 1/1995 |
| JP | A-7-171211 | 7/1995 |
| JP | A-8-332217 | 12/1996 |
| RU | 2 133 595 | 7/1999 |
| SU | 1 818 091 | 5/1993 |
| WO | WO 91/06324 | 5/1991 |
| WO | WO 93/20857 | 10/1993 |

* cited by examiner

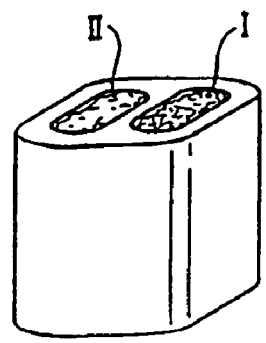
FIG. 4
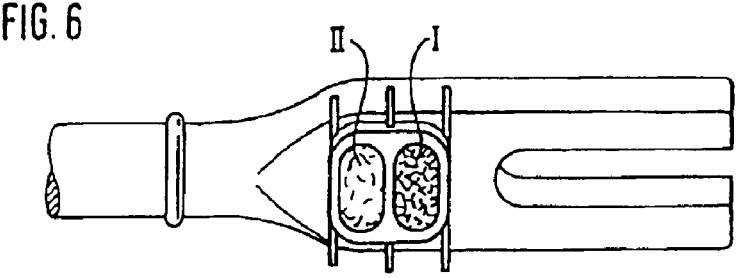
FIG. 6
FIG. 5a    FIG. 5b    FIG. 5c
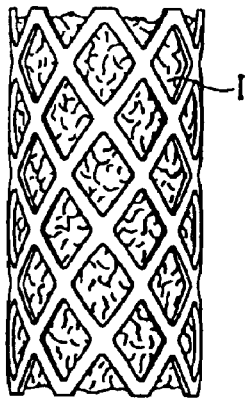 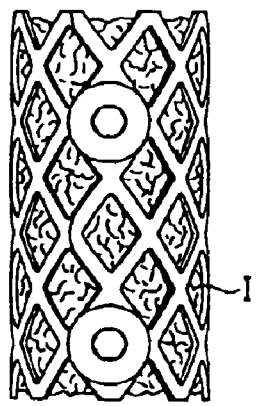 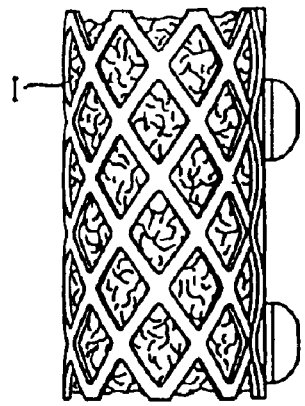

IMPLANT FOR RECREATING VERTERBRAE AND TUBULAR BONES

This application is a continuation-in-part (CIP) of application Ser. No. 09/295,302, filed Apr. 21, 1999; which is a CIP of application Ser. No. 08/899,270, filed Jul. 23, 1997, now U.S. Pat. No. 5,928,635, which was a file-wrapper-continuation (FWC) and is a CIP of application Ser. No. 08/313,113, filed Dec. 7, 1994 now abandoned, which claims priority of application Ser. No. 07/849,083, filed Sep. 19, 1992; and which is a CIP of application Ser. No. 08/350,666, filed Dec. 7, 1994, now U.S. Pat. No. 5,932,207, which is a continuation of application Ser. No. 07/849,083 filed on Sep. 17, 1992, now abandoned; the specifications of which are incorporated herein by reference.

FIELD OF THE INVENTION

The invention relates to an implant which comprises an active substance complex with the following components which differ from one another, namely at least one structural component, at least one recruiting component, at least one adhesion component, and at least one growth and/or maturation component.

BACKGROUND OF THE INVENTION

An active substance complex for creating biological parts, in particular organs for living organisms, with said components is already known in the prior art. In this known active substance complex, the structural component can consist for example of different collagens, elastin or proteoglycans. As recruiting component for this active substance complex, chemotactics may be mentioned in particular, for example peptides, such as N—F-Met-Leu-Phe- and/or for example metabolites of arachidonic acid, such as leukotrienes. The role of the adhesion component can be played by proteins of the fibronectin or laminin type, but also by cell adhesion molecules, such as L-CAM, N-CAM, and matrix adhesion molecules, such as cytotactin, tenascin, collagen types IV, V, VII, synthetic peptides and transmembrane compound proteins, such as integrin. For the purposes of the active substance complex discussed here, the first-mentioned examples of adhesion components, namely fibronectin and laminin, are to be classed as matrix adhesion molecules. As a further component, said active substance complex comprises at least one growth and/or maturation component, preferably in the form of one or more cytokines. Examples of such cytokines are colony-stimulating factors in the production of blood; fibroblast growth factor in the production of connective tissue; epidermal growth factor in the production of skin; cartilage-inducing factor in the production of cartilage; lymphocyte-activating factor and spleen peptides in the production of spleen or lymph nodes; T-cell growth factor and thymus peptides for the production of thymus; bone growth factor and transforming growth factor for the production of bone; and angiogenesis factor for the production of blood vessels. The following cytokines are also used: interleukins, insulin-like growth factors, tumor necrosis factor, prostaglandins, leukotrienes, transforming growth factors, platelet-derived growth factor, interferons, and endothelium-derived growth factor.

More details concerning this active substance complex are to be found in European Patent No. 0,500,556, the content of which is expressly included in the present document.

Following its production, this active substance complex initially has a cottonwool consistency. If large bone defects are to be filled, the active substance complex introduced as an implant must have sufficient inherent strength to ensure that it is not compressed by the surrounding soft tissues or bone structures. It must therefore already be compressed prior to said use, which results in greater mechanical strength but also a high consumption of material, or else a sufficiently stable support material must be used together with the active substance complex. However, the combination of a support material with the active substance complex is by no means unproblematic. Based on previous experience of the active substance complex and of its complex mode of action, one would have to expect at least a reduced formation or recreation of the particular biological part to be treated, for example osseous regeneration. The risk of a histotoxic reaction has also been suspected.

In addition, it has not hitherto been possible to use the active substance complex for diseases or defects in which the implant consisting of the active substance complex is subjected to such high mechanical stresses that even the mechanical strength of a compressed material can be insufficient.

SUMMARY OF THE INVENTION

Based on the above, it was therefore an object of the present invention to make available an implant with which a high mechanical strength is achieved, in order thereby to extend the range of possible uses of the active substance complex.

This object is achieved by means of an implant in which a metallic, nonmetallic or ceramic hollow body is coated with said active substance complex or comprises this active substance complex, as a result of which an implant is obtained which can be used for at least partially creating, recreating or stabilizing vertebral bodies or tubular bones. The components of the active substance complex are here adapted for creating bone, which also includes forming all the structures supplying the bone or vertebra, for example the blood vessels and nerves.

The solution to this object was not obvious since, as has already been explained, it is extremely problematic to combine the active substance complex and a support with which the active substance complex is coated or which it comprises, because the functions of the active substance complex, for example in the bone defect, could then be disturbed or at least complicated by possible immune reactions.

The metallic hollow body consists preferably of titanium, also in the form of titanium alloys. An alloy of titanium, aluminum and vanadium was examined in particular. In a preferred embodiment, the metallic supports are used in the form of cylindrical hollow bodies with a lattice structure.

The principal nonmetallic material to be mentioned here is carbon, which can be used in the form of "carbon cages", consisting of carbon fibers, and which can also form cylindrical hollow bodies. Both the titanium (hollow) bodies and the carbon cages are filled with the active substance complex or are coated with the active substance complex on their inside surface.

When they have been filled or coated with the active substance complex, said titanium hollow bodies and carbon cages can be used to create, recreate or stabilize vertebral bodies. This affords the unique possibility of repairing vertebral defects or damaged vertebrae of the spinal column by interlocking of vertebral bodies and complete regeneration of the vertebra.

Interlocking of vertebral bodies is often necessary when degenerative processes of the intervertebral disks, tumors or metastases in the vertebral bodies of the spinal column, or even osteoporosis, have impaired the load-bearing capacity of the spinal column, with the result that there is a threat either of spinal fractures or of nerve lesions. In these cases it is necessary to secure the continuity of the spinal column using a mechanically stable implant such as the titanium body or carbon cage. The osseous bridging required for this could hitherto only be attempted using autologous spongy substance, for example spongy substance from the iliac crest, obtained in a second intervention. This entailed a series of problems, for example the secondary intervention and the associated operating risk, with an additional danger of infection, the limited quantity of recoverable spongy substance and complications at the donor site, such as infections or chronic pain conditions. The availability of such autografts is also limited.

By filling or coating the titanium hollow bodies or carbon cages with the active substance complex, it was possible to achieve osseous bridging in a short time without the need for autologous spongy substances. The lattice structure of the titanium hollow body also permitted rapid vascularization in the inside of the dimensionally stable component, so that the active substance complex can exert its activity and bone formation takes place across the whole of the necessary volume without mechanical forces impairing the form of the newly generated bone. In addition to the use in the area of the vertebral bodies, such a titanium hollow body or carbon cage, and also the ceramic hollow bodies described below, can also be used at any other desired implantation sites, for example in the jaw, on tubular bones, and in principle for augmentation of bone mass. With the active substance complex available hitherto, interlocking of vertebrae was not possible because the active substance complex would not have been able to withstand the mechanical stressing within the spinal column. The hollow bodies or cages now filled or coated with the active substance complex afford mechanical stability, but without causing immunological counter-reactions or impairing the efficacy of the active substance complex.

In addition to metallic or nonmetallic hollow bodies, it is also possible to use hollow bodies made of ceramic materials. Ceramic support materials which may be mentioned are in particular glass ceramics, such as calcium phosphate ceramics, aluminum oxide ceramics, and hydroxylapatite ceramics.

The calcium phosphate ceramics are based on the CaO/$P_2O_5$ system. On the basis of this system there are five different binary compounds. Of these, tricalcium phosphate (TCP) and tetracalcium phosphate have proven suitable for the proposes of the invention.

TCP is prepared by pressing and subsequently sintering the starting materials calcium oxide (CaO) and diphosphorus pentoxide ($P_2O_5$). Alternatively, it can also be prepared in a hot-pressing step.

Tetracalcium phosphate, like TCP, is prepared in two steps by means of the starting materials first being compacted to a crystal-lattice spacing of 5 to 10 $\mu$m and the composition then being fired at 1100 to 1500° C.

Hydroxylapatite is obtained by ceramic firing of pentacalciumhydroxide triphosphate power at 1250° C. In addition, a hydroxylapatite ceramic can also be produced using a natural material such as the carbonate skeleton of red alga. After a washing and drying procedure, the organic constituents are first removed by pyrolysis at a temperature of about 700° C. This is followed by conversion to hydroxylapatite by addition of phosphate solution at elevated pressure and increased temperature.

In a further method for producing a hydroxylapatite ceramic, starting from the natural skeleton of corals, the calcium carbonate of the corals is converted by hydrothermal conversion to hydroxylapatite or a mixture of hydroxylapatite and other mineral structures. In the material thus obtained, the coralline structure, i.e. in particular the interconnecting pore system of the coral, is preserved.

Aluminum oxide ceramics which have a polycrystalline structure contain about 99.7% aluminum oxide and also small amounts of magnesium oxide and/or zirconium oxide. After precompression at high pressure, they are sintered at temperatures of about 1500 to 1800° C. to give a solid body. For the purposes of the present invention, microporous aluminum oxide ceramics were used. Monocrystalline forms (sapphires) can also be used.

The active substance complex itself can additionally be applied to support materials which are selected from polymers and collagens. The amount of active substance complex required to fill the respective hollow body can be reduced in this way in order to minimize costs while at the same time maintaining substantially the same bone-forming efficacy.

The polymer support materials which can be used are in particular polymers of natural monomers, such as polyamino acids (polylysin, polyglutamic acid, etc.), and polymers of lactic acid. Copolymers can also be used, for example of polylactic acid and hydroxyacetic acid.

Polylactates are polyesters of lactic acid having the chemical formula:

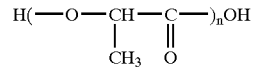

Direct polymerization of the monomers results in polymers with relatively low molecular weights. The upper limit is about 20 000 Da. Higher molecular weights can result by linking of cyclic dimers at high temperature and low pressure and in the presence of catalysts. Lactic acid polymers are biodegradable, biocompatible, insoluble in water, and characterized by a high degree of strength.

Different collagens can also be used as support material. Collagens of types I, IV, V and VII may be mentioned here in particular. The collagens can be used for example in the form of webs or gels, and they in particular have an inherently good immunological compatibility and are easy to process.

BRIEF DESCRIPTION OF THE DRAWINGS

The invention is explained in greater detail below on the basis of examples and with reference to the attached drawing, in which:

FIG. 4 shows a diagrammatic representation of a hollow body made of carbon fibers without a lattice structure, with two chambers for comparison between active substance complex and autologous spongy substance, FIGS. 5a–c show diagrammatic representations of a hollow body made of titanium, with a lattice structure, which is filled with the active substance complex and is used to interlock vertebral bodies, FIG. 6 shows a cage insertion device which has a carbon cage with two chambers.

DETAILED DESCRIPTION OF THE INVENTION

I. Preparation of the Active Substance Complex

The main steps in the preparation of the active substance complex are described below:

Tubular bones from calves, sheep, rabbits or rats were cleaned, the bone marrow, inter alia, was removed, and the bones were then frozen. The frozen bone was ground to a particle size of less than 2 mm. The ground bone pieces were defatted in acetone and decalcified in 0.6 N hydrochloric acid. The product was then freeze-dried and a demineralized bone matrix was obtained which was extracted in 4 molar guanidium-HCl solution. The extraction solution was dialyzed against distilled water and the active substance complex was obtained by centrifuging off and freeze-drying in the precipitate.

This basic method of preparation is shown below.

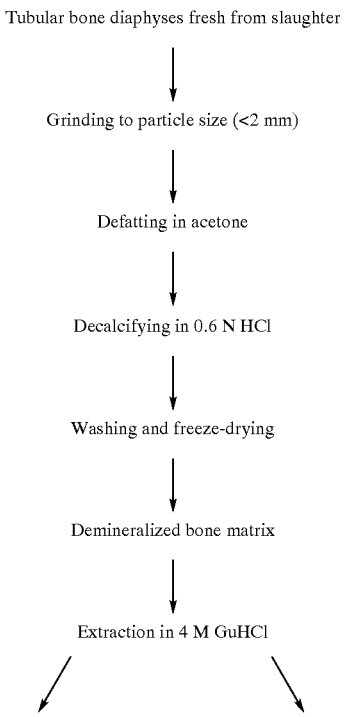

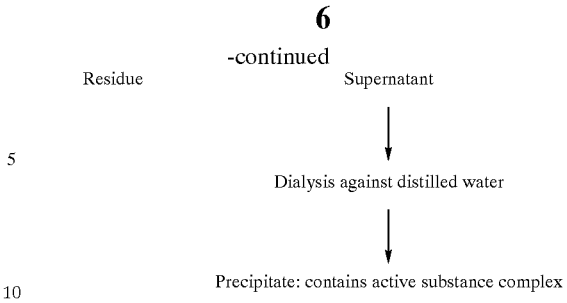

II. Efficacy of the Active Substance Complex without Use of Support Materials

To show that the active substance complex is effective per se, a test is first set out in which the active substance complex is implanted without additional supports or support materials.

1. Animals Used in the Test

Female chinchilla rabbits with a mean bodyweight of 3089 g were used. They received a rabbit maintenance diet and double-ozonized tap water acidified with hydrochloric acid to pH 4.5 ad libitum.

The animals were anaesthetized by subcutaneous injection of a mixture of ketamine and xylazine.

2. Preparation of a Bone Defect in the Rabbits

An internally cooled drill was used to prepare an implant bed of 4 mm diameter and circa 9 mm depth in the knee joint (distal end of femur) of the rabbit. The bore hole thus formed was then filled in each case with 30 and 90 mg of the active substance complex which had been produced as described under I. A further bore hole in each case was left untreated and served as a control for new bone formation.

Figure 1:
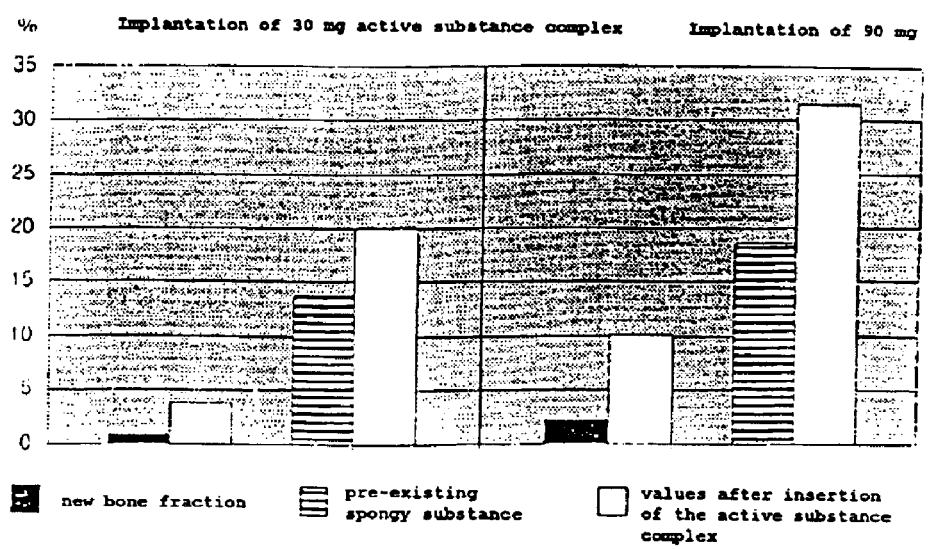
FIG. 1 shows a diagrammatic representation of new bone formation in rabbits using the active substance complex, compared with an untreated sample.

FIG. 1 shows the new bone formation in the untreated hole and in the bore hole after. implantation of the active substance complex and also the density of the surrounding pre-existing spongy substance 28 days after the operation (n=2/active substance quantity).

Analysis of the tests revealed that the density of the spongy substance surrounding the bore holes after implantation of 30 mg of the active substance complex was 45% higher than in the untreated hole, and, after implantation of 90 mg of the active substance complex, was 69% higher than in the untreated hole. The quantity of pre-existing spongy substance had no influence at all on the regeneration in the defect because the new bone formation after insertion of the active substance complex did not start from the periphery of the bore hole but instead was distributed uniformly across the defect.

III. Bone Formation in the Mandible of Sheep Using Tricalcium Phosphate (TCP)

1. Animals Used for the Tests

Fully grown domestic sheep from Viehzentrale Sudwest AG of Stuttgart were used in the tests described below. They were supplied with hay and water and, three days before the operation, a slurry of Altromin pellets.

The animals were premedicated with 1 ml xylazine/1 ml ketanest i.m. The sheep were then anesthetized with Nembutal.

2. Preparation of the Implant

TCP was suspended in a solution of 100 mg of dissolved active substance complex with 10 ml of water and deep-frozen with liquid nitrogen under constant stirring. After 24 hours of freeze-drying and subsequent gas sterilization (ethylene oxide), the TCP thus doped with the active substance complex was introduced into the mandibular defect described below in a sheep. In addition, a further mandibular defect serving for comparison purposes was filled with undoped TCP sterilized in an autoclave.

3. Preparation of the Mandibular Defect in Sheep

A sheep mandible was suitably prepared and, with physiological saline solution as coolant, a trephine of 5 mm diameter was used to cut out and remove in each case a standardized cylinder of bone. One of the bore holes thus formed was then filled with TCP, which had been doped with the active substance complex according to test procedure 1, and the second bore hole was filled with undoped TCP.

Figure 2:
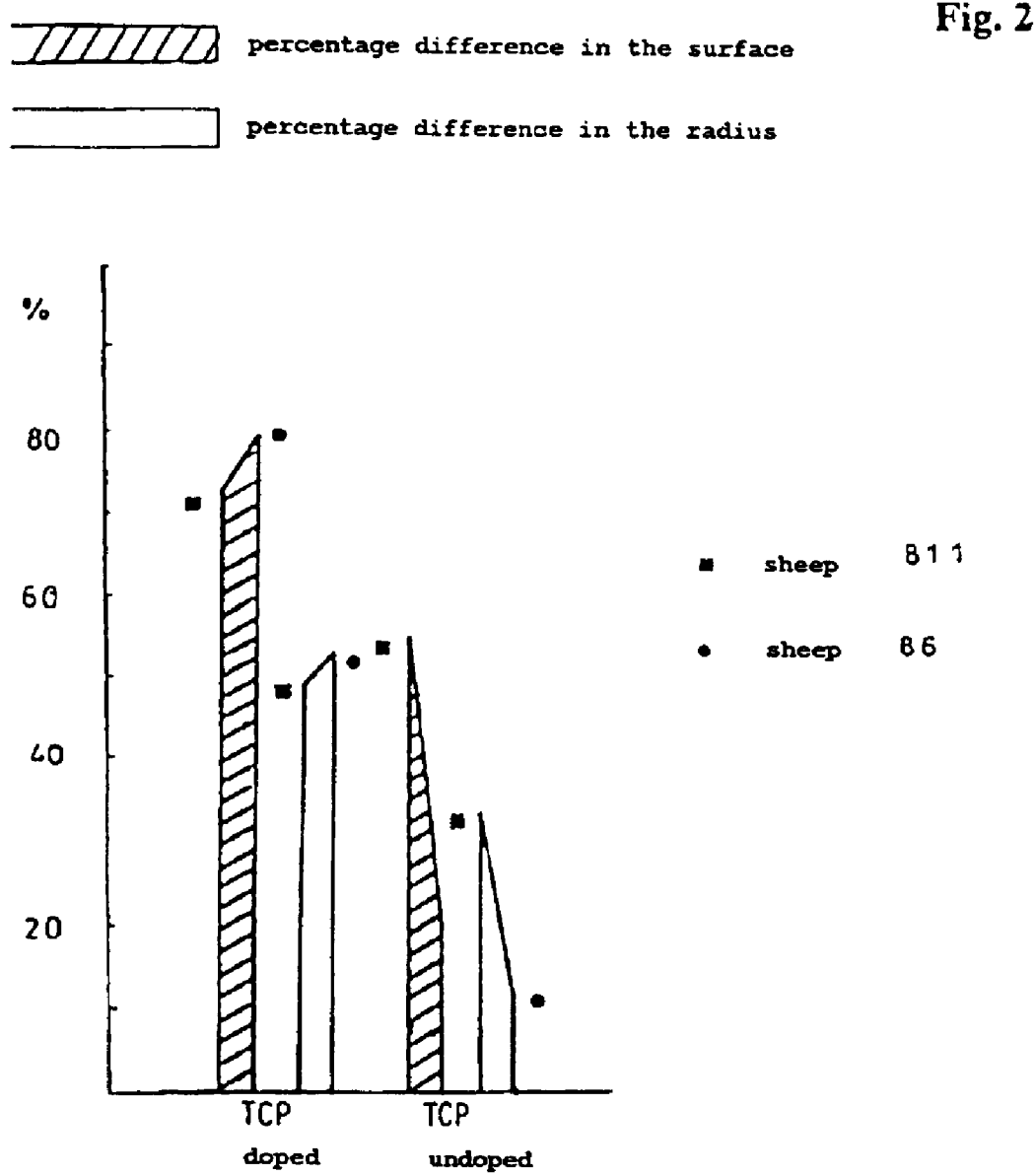
FIG. 2 shows a diagrammatic representation of new bone formation in sheep using the active substance complex, with tricalcium phosphate as support material, compared with pure tricalcium phosphate.

For purposes of clarity, the results of the bone growth in the mandibular defects are shown in graph form in FIG. 2. The test duration was 26 days and 41 days respectively.

It was found that doping TCP with the active substance complex accelerated bone regeneration of the mandibular defect in both sheep No. 811 and No. 86 by about 100% in the initial phase. After 41 days, the rate of acceleration of bone regeneration was still 10%. Bone healing is therefore much more rapid, particularly at the start, than it is without the osteoproductive effect of the implants doped with the active substance complex.

IV. Tests with Collagens as Support Materials

In the production of the active substance complex, the quantitative yield at the required degree of purity is very low. We therefore examined whether there are support materials which can be combined with the active substance complex so as to be able to reduce the quantity of active substance complex needed for the particular objective, but without thereby reducing its bone-forming efficiency.

1. Active Substance Complex

The active substance complex used for the purposes of the tests described below was prepared exactly in the manner described under I., using tubular bones from calves.

2. Animals Used in the Tests

Male Wistar rats weighing between 350 and 400 g were used and were kept in an air-conditioned animal housing at 23° C. and about 50% relative humidity. They were given a maintenance diet for rats and mice.

Two implants of the same support material were introduced into the abdominal musculature of each test animal, of which one implant was coated with the active substance complex while the other remained uncoated and served as a comparison implant. The animals were sacrificed after 21 days, and the affected areas of the implants in the abdominal musculature were explanted and histologically evaluated.

3. Support Materials Used

In these tests, collagen materials were used which are all commercially available. Collagen A was a pure, sterile, native, resorbable bovine skin collagen, free from any foreign additives such as stabilizers or disinfectants.

Collagen B was a purified, freeze-dried, lightly crosslinked sterile and nonpyrogenic bovine skin collagen with weakly antigenic properties. The helical structure of the collagen was preserved.

Collagen C comprised pure, native and resorbable bovine collagen fibrils.

Figure 3:
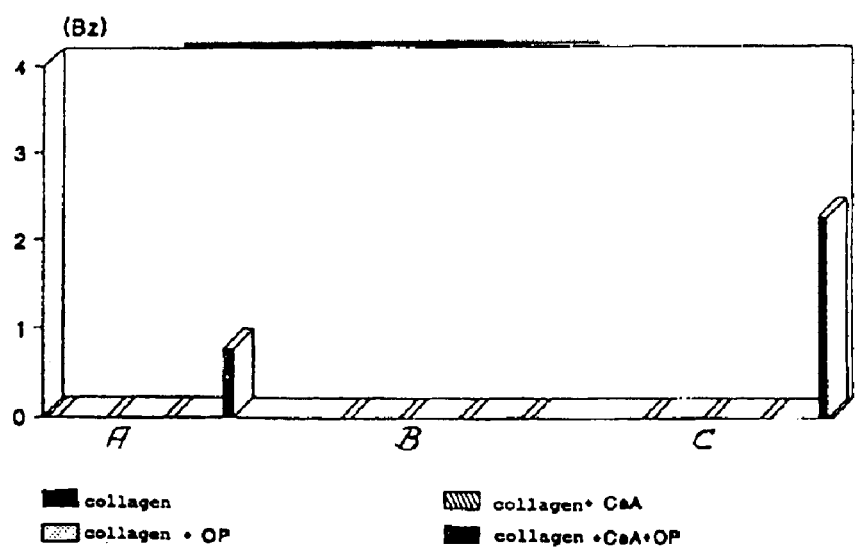
FIG. 3 shows a diagrammatic representation of new bone formation in rats using the active substance complex, with different collagens as support material, compared with pure collagens.

All the collagens used were in web form. Collagen web sections each of 50 mg were cut out, and 1 ml of the active substance complex solution (3 mg/ml) was added in each case. In the control implants, 1 ml of distilled water was added instead. The collagen web sections thus treated were frozen at ~20° C., freeze-dried and yielded implants with a diameter of about 10 mm and a thickness of about 5 mm. FIG. 3 shows the bone formation results for collagen implants A, B and C in immunosuppressed animals and non-immunosuppressed animals after 21 days, with and without coating with the active substance complex (cyclosporin A). Here, the evaluation figure (BZ) corresponds to the arithmetic mean of the evaluation figures from three independent persons on six implants of each group.

Collagen A coated with the active substance complex showed a bone formation effect in immunosuppressed animals after this period of time, whereas this could not be demonstrated for collagen B. By contrast, however, collagen C showed a very pronounced bone formation effect.

It follows from this that it depends on the preparation of the particular collagen used and this dictates its suitability as a support material. Collagens which are immunogenic are not suitable for use as support materials.

IV. Testing Metallic and Ceramic Materials for their Biocompatibility

Titanium disks of different surface roughness (100, 20 and 0.5 $\mu$m), a TiAl$_6$V$_4$ alloy (0.5 $\mu$m) and Al$_2$O$_3$ disks from the company Friedrichsfeld and hydroxylapatite disks from Feldmühle AG were used.

The coatings with the active substance complex, which had been prepared from tubular bones of calves using the general procedure set out above, were applied by the dip-coating method. Dip-coating is understood as a coating method in which the object to be coated, in this case the disks, is dipped into a solution with a desired predetermined concentration of the coating agent, in this case the active substance complex. This is followed by freeze-drying. Thin cover layers or coatings are obtained. The testing of the specified materials for their biocompatibility was carried out in particular with reference to the surface roughness (n=20; four disks each). Table 1 shows the results obtained.

This biocompatibility testing of the materials under investigation revealed that titanium, with the highest number of living cells and the best ratio of living cells to dead cells, is very well suited as a support material. While hydroxylapatite provided a similarly good result, TiAl$_6$V$_4$ was considerably poorer.

Generally, as regards surface roughnesses, it was found that the smoothest surfaces, i.e. surfaces with a pore diameter of 0.2–0.5 $\mu$m, yielded the best results, with the exception of TiAl$_6$V$_4$. As the roughness or pore diameter increases, the number of living cells and also the ratio of living cells to dead cells drop. The highest proportion of living (bone) tissue in direct contact with the disk surface was obtained with a pore diameter of about 0.5 $\mu$m.

TABLE 1

| Support material | Number of living cells per cm$^2$ | Number of dead cells per cm$^2$ |
| --- | --- | --- |
| Hydroxyl apatite | | |
| 0.2–0.5 $\mu$m | 1792 ± 700 | 200 ± 37 |
| 20 $\mu$m | 7469 ± 2614 | 2238 ± 715 |
| 50 $\mu$m | 4477 ± 408 | 1692 ± 427 |
| Osprovit (Feldmühle) | 7930 ± 2007 | 1638 ± 377 |
| Titanium | | |
| 0.5 $\mu$m | 11377 ± 2538 | 1054 ± 308 |
| 20 $\mu$m | 9600 ± 3038 | 1754 ± 439 |
| 100 $\mu$m | 2308 ± 669 | 2085 ± 623 |
| TiAl$_6$V$_4$ 0.5 $\mu$m | 7200 ± 1062 | 2800 ± 954 |
| Al$_2$O$_3$, extra pure, polished | 11446 ± 1500 | 2292 ± 600 |

V. Titanium Bodies and Carbon Cages

As the tests described under IV. had demonstrated the essential biocompatibility of titanium, this pointed to a particular use of the active substance complex in dimensionally stable titanium cages for interlocking the vertebral bodies (spondylodesis). In addition, carbon cages were also found to be suitable for this purpose.

As regards spondylodesis, a surgical intervention was able to be performed on the spinal column of a human subject, which permitted a comparison between the use of autologous spongy sunbstance and the active substance complex.

A carbon cage with two chambers was used for this purpose. Such a carbon cage is shown diagrammatically in FIG. 4. Instead of the carbon cage, it is equally possible to use a titanium hollow body which is shown diagrammatically in FIGS. 5a, b and c. FIGS. 5a–5c show different views of the titanium hollow body filled with the active substance complex.

For the tests concerned here, a carbon cage without a lattice structure was used because this was available with two chambers (I, II) for receiving, on the one hand, the active substance complex and, on the other, the autologous spongy substance as a comparison.

The active substance complex used was obtained from calf bones, as is described under I., and introduced into a chamber (I) of the carbon cage, while the other chamber (II) was filled with autologous spongy substance from the patient to be treated. The carbon cage thus prepared was fitted in the area of spinal segment L5/S1 (lumbar spine in the area of the intervertebral disks) using a cage insert device. The insert device already provided with the carbon cage is shown in FIG. 6. The right-hand chamber (I) in the figure contains the active substance complex, and the left-hand chamber (II) contains the autologous spongy substance.

Figure 7A:
FIGS. 7a–b show X-rays of a greatly reduced lumbar spacing at segment L5/S1 before the operation.
Figure 7B:
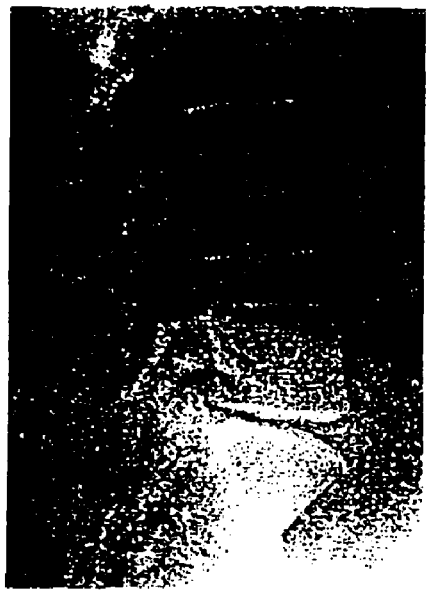
Figure 8B:
FIGS. 8a–b show X-rays of an implant between vertebrae L4 and L5 of the lumbar spine, with the internal fixator fitted for stabilization.
Figure 8A:
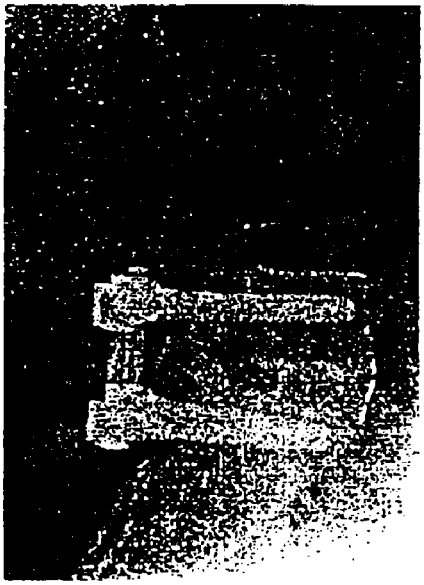

FIGS. 7a and 7b show the greatly reduced space between L5 and S1 prior to insertion of the implant. FIGS. 8a and 8b show the support offered by the inserted implant between vertebrae L4 and L5 and the internal fixator introduced for stabilizing purposes.

Figure 9:
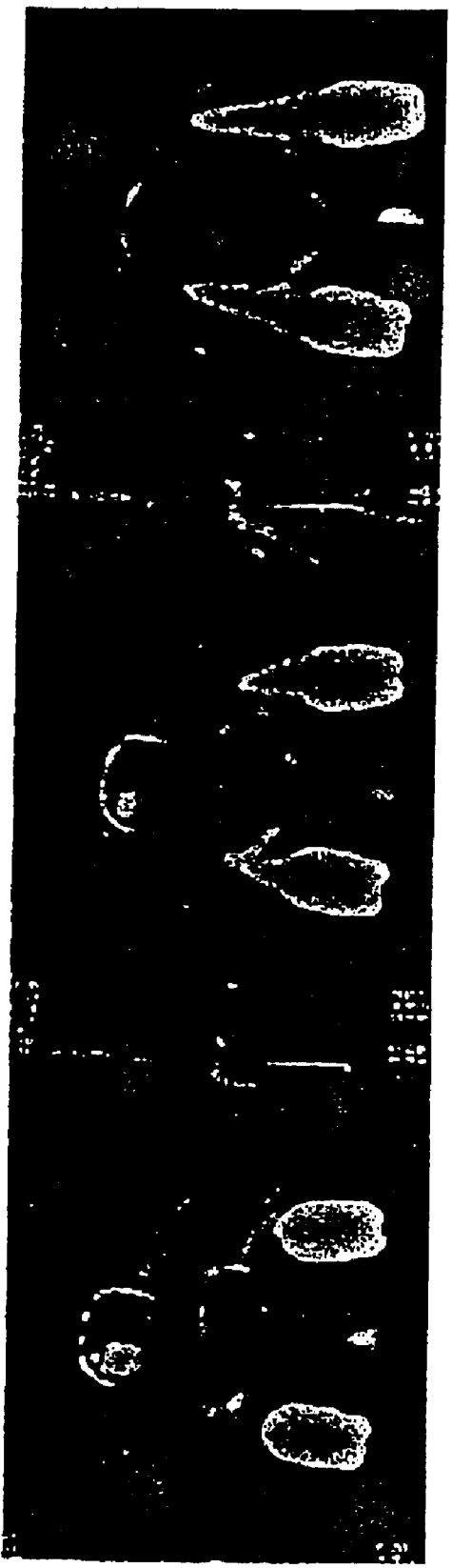
FIG. 9 shows a sequence of images obtained by computed tomography at three, six and nine weeks after fitting of a carbon cage implant, with active substance complex and autologous spongy substance.

FIG. 9 shows, viewed from left to right, an image sequence obtained by computed tomography three, six and nine weeks after fitting of the cage implant. The left-hand chamber of the cage contains the autologous spongy substance and the right-hand chamber contains the active substance complex. It can be clearly seen that in the left-hand chamber with spongy substance the X-ray density continuously decreases, this being a sign of bone loss, while in the right-hand chamber with the active substance complex it increases over the entire period, this being a sign of bone growth. After nine weeks, the implant according to the invention shows an at least equal result through bone formation as the autograft assessed according to the prior art as the "gold standards" through bone loss. When using the implant according to the invention, no risk-associated second intervention is necessary, and no time is needed for primary bone loss.

Table 3 shows the measured optical density for the tests represented graphically in FIG. 9.

TABLE 3

| Optical density of mineralized bone in the implant [%] | | | |
|---|---|---|---|
| | 3 weeks | 6 weeks | 12 weeks |
| Autologous spongy substance | 100 | 42 | 26 |
| Active substance complex | 4 | 12 | 28 |

What is claimed is:

1. An implant for at least partially creating, recreating or stabilizing vertebral bodies or tubular bones, said implant having a metallic, non-metallic, or ceramic hollow body which is coated with an active substance complex or comprises said active substance complex, said active substance complex comprising the following components:
   at least one structural component based on extracellular material which is specifically adapted to cells of the bone to be created;
   at least one recruiting component;
   at least one adhesion component; and
   at least one growth and/or maturation component, wherein the components differ from one another and are specifically adapted for creating bone.

2. The implant of claim 1, wherein the metallic hollow body is composed of titanium or titanium alloy.

3. The implant of claim 1, wherein the metallic hollow body is configured in the form of a cylinder with a lattice structure.

4. The implant of claim 1, wherein the non-metallic hollow body is composed of carbon fibers.

5. The implant of claim 1, wherein the ceramic hollow body is composed of calcium phosphate, aluminum oxide, or hydroxylapatite ceramic.

6. The implant of claim 1, wherein the hollow body is filled with the active substance complex being applied to support materials which are selected from polymers and collagens.

* * * * *